United States Patent [19]

Kulprathipanja

[11] Patent Number: 5,453,560
[45] Date of Patent: Sep. 26, 1995

[54] PROCESS FOR ADSORPTIVE SEPARATION OF ETHYLBENZENE FROM AROMATIC HYDROCARBONS

[75] Inventor: Santi Kulprathipanja, Inverness, Ill.

[73] Assignee: UOP, Des Plaines, Ill.

[21] Appl. No.: 247,176

[22] Filed: May 20, 1994

[51] Int. Cl.⁶ ..................................................... C07C 7/12
[52] U.S. Cl. ............................................ 585/828; 585/831
[58] Field of Search ..................................... 585/828, 831

[56] References Cited

U.S. PATENT DOCUMENTS

| | | | |
|---|---|---|---|
| 3,867,470 | 2/1975 | Van Grinsven et al. | 260/674 SA |
| 3,943,182 | 3/1976 | Neuzil et al. | 260/674 SA |
| 4,593,149 | 6/1986 | Barthomeuf | 585/828 |
| 4,886,929 | 12/1989 | Neuzil et al. | 585/828 |

*Primary Examiner*—Sharon A. Gibson
*Assistant Examiner*—Nhat D. Phan
*Attorney, Agent, or Firm*—Thomas K. McBride; John F. Spears, Jr.

[57] ABSTRACT

Ethylbenzene is recovered from a mixture of $C_8$ aromatic hydrocarbons including xylenes by adsorptive separation in a narrow temperature range using a cesium exchanged X zeolite as the adsorbent. A mixture of diethylbenzene and toluene is the preferred desorbent.

9 Claims, No Drawings

PROCESS FOR ADSORPTIVE SEPARATION OF ETHYLBENZENE FROM AROMATIC HYDROCARBONS

BACKGROUND OF THE INVENTION

1. Field of the Invention

This invention relates to the separation of ethylbenzene from complex admixtures of aromatic hydrocarbons including xylenes. The invention more directly relates to the recovery of ethylbenzene by selective adsorption using certain crystalline aluminosilicate zeolitic molecular sieves. The invention relates specifically to the operating temperature and desorbent composition which provide unexpected benefits.

2. Related Art

Those skilled in the art are familiar with a number of adsorptive separation methods which may be employed to perform the separation of aromatic hydrocarbons. The separation of $C_8$ aromatics using zeolitic adsorbents has been described in the literature. For instance, U.S. Pat. No. 3,867,470 issued to P. F. A. Van Grinsven et al. is directed to the adsorptive separation of ethylbenzene from a mixture of C8 aromatic hydrocarbons using a Faujasite X which may be exchanged with cesium ions.

U.S. Pat. No. 3,943,182 issued to R. W. Neuzil and D. H. Rosback describes the use of zeolite X which has been ion exchanged with a Group I-A metal which may be cesium to recover ethylbenzene from admixture with xylenes. Accompanying this disclosure is a discussion of the use of paradiethylbenzene or mixtures of p-diethylbenzene and benzene as a desorbent, and the importance of such operational parameters as the silica to alumina ratio of the zeolite and the amount of water on the zeolite as measured by loss on ignition (LOI) techniques.

U.S. Pat. No. 4,593,149 issued to D. M. Barthomeuf also describes the recovery of ethylbenzene from ethylbenzenexylene mixtures through the use of a cesium exchanged X zeolite. This reference broadly describes suitable individual desorbents including diethylbenzene and toluene.

BRIEF SUMMARY OF THE INVENTION

The invention is an improved adsorptive process for separating ethylbenzene from a mixture containing ethylbenzene and xylenes. The improvement is derived from the discovery of unexpected discontinuity in the normal stage-time/selectivity/temperature correlations in a narrow temperature range. Unexpected synergistic benefits have also been found to result from the use of a mixture of two desorbent compounds. The process employs an adsorbent comprising a low silica zeolite X which has been at least partially exchanged with cesium. The adsorbent is also characterized by a low water content. Diethylbenzene and/or toluene is employed as the desorbent.

One embodiment of the invention may be characterized as a process for separating ethylbenzene from a mixture comprising ethylbenzene and at least one other $C_8$ aromatic hydrocarbon, which process comprises contacting said mixture at adsorption conditions including a temperature between about 100° and 125° C. with an adsorbent comprising a cesium exchanged zeolite X having a silica:alumina ratio from about 2.0:1.0 to about 2.3:1.0, selectively adsorbing said ethylbenzene, removing the nonadsorbed portion of said mixture from contact with said adsorbent and recovering ethylbenzene by desorption with a desorbent comprising paradiethylbenzene at desorption conditions.

DETAILED DESCRIPTION OF THE INVENTION AND PREFERRED EMBODIMENTS

Ethylbenzene is a valuable commercial commodity used in the manufacture of a number of useful products. For instance, it may be dehydrogenated to produce styrene for use in plastics. The main industrial route to the production of ethylbenzene is the alkylation of benzene. However, the effluent of the typical naphtha reforming zone contains a high concentration of aromatic hydrocarbons and there have been proposals to recover ethylbenzene from aromatic-rich hydrocarbon mixtures derived from these reformates by adsorption in the same manner xylenes are now recovered. It has also been suggested to recover ethylbenzene from the process streams circulating in xylene isomerization units prior to or subsequent with the recovery of desired xylene isomers. However, the adsorptive recovery of ethylbenzene has not been a commercial success and much ethylbenzene in these sources is simply converted to other materials such as benzene or xylene or sold in gasoline.

It is an objective of the subject invention to provide an improved process for the adsorptive separation of ethylbenzene from other monocyclic aromatic hydrocarbons. It is a further objective to provide an adsorptive process for the recovery of ethylbenzene from xylene-rich hydrocarbon fractions.

These objectives are achieved through the use of a desorbent comprising a low silica zeolite X, a novel desorbent system and specific process conditions. The type X zeolite is generally described in U.S. Pat. No. 2,882,244. The framework silica:alumina ratio of the X zeolite used in the subject process must be below about 2.3:1 and should be less than about 2.2:1 preferably less than about 2.1:1. Cesium-exchanged X zeolite having a 2.0:1 silica:alumina ratio was found to have a larger pore radius (14.00 vs. 12.93Å) and lower Langmuir surface (536 vs. 573 m/g) and volume (115 vs. 124 cc/g) than an equivalent 2.5:1 ratio X zeolite. How these factors contribute to better performance is not fully understood.

It is important that the zeolite X molecular sieve is ion exchanged to replace a large percentage of the native sodium with cesium ions. Exchange methods well known to those skilled in the art are suitable for the zeolites of this invention. It is preferred that at least about 40 mole percent of the sodium ions are replaced by cesium ions and more preferably that at least about 50 to about 60 percent of the sodium ions are replaced by cesium ions. Further information on the effect of cesium is given in Example 4 below. Suitable zeolite X materials are available from UOP of Des Plaines, Illinois, U.S.A.

Those skilled in the art will appreciate that the performance of an adsorbent is greatly influenced by a number of factors not related to its composition such as operating conditions, feed stream composition, water content and desorbent composition. The optimum adsorbent composition is therefore dependent upon a number of interrelated variables. One such variable is the water content of the adsorbent which is expressed herein in terms of the recognized Loss on Ignition (LOI) test. For instance Neuzil, cited above, reported that the ability of an X zeolite to adsorb ethylbenzene increased and its ability to reject xylenes decreased as the amount of water in the zeolite increased. In the LOI test the volatile matter content of the zeolitic adsorbent is determined by the weight difference obtained before and after drying a sample of the adsorbent at 900° C. under an inert gas purge such as nitrogen for a period of time sufficient to achieve a constant weight. The difference in weight, calculated as a percentage of the sample's initial weight, after being calcined for 2 hours at 400° C., is reported as loss on ignition at 900° C. and represents the volatile matter present within the adsorbent. It is preferred that the water content of the adsorbent results in a LOI at 900° C. of less than 0.5% and preferably within the range of from 0.5 to 0.2 wt. %.

Typically, the adsorbent particles used in separation processes contain small zeolite crystals dispersed in an amorphous material or inorganic matrix such as clay used in forming the particles. The zeolite will ordinarily be present in the adsorbent particles in amounts ranging from about 75 to about 98 wt. % based on volatile-free composition. Volatile-free compositions are generally determined after the adsorbent has been calcined at 900° C. in order to drive off all volatile matter. The remainder of the adsorbent will generally be the inorganic matrix material such as silica, titania, or alumina or mixtures thereof, or compounds, such as clays, which are present in intimate mixture with the small particles of the zeolite material. This matrix material may be an adjunct of the manufacturing process for the zeolite (for example, from the intentionally incomplete purification of the zeolite during its manufacture) or it may be added to relatively pure zeolite, but in either case its usual purpose is as a binder to aid in forming or agglomerating the zeolite into hard crystalline particles, such as extrudates, aggregates, tablets, macrospheres or granules having a desired particle size range. The typical adsorbent will have a particle size range of about 16–60 mesh (Standard U.S. Mesh).

In the present invention the separation of ethylbenzene is effected by passing a feed mixture over a bed of an adsorbent which selectively adsorbs the ethylbenzene while permitting other components of the feed stream to pass through the adsorption zone in an unchanged condition. The flow of the feed is stopped and the adsorption zone is flushed to remove nonadsorbed materials surrounding the adsorbent. Thereafter the ethylbenzene is desorbed from the adsorbent by passing a desorbent stream through the adsorbent bed, with the desorbent material preferably comprising an aromatic hydrocarbon. The desorbent material is commonly also used to flush nonadsorbed materials from the void spaces around and within the adsorbent.

For purposes of this invention, various terms used herein are defined as follows. A "feed mixture" is a mixture containing one or more extract components and one or more raffinate components to be separated by the process. The term "feed stream" indicates a stream of a feed mixture which passes to the adsorbent used in the process. An "extract component" is a compound or class of compound that is more selectively adsorbed by the adsorbent while a "raffinate component" is a compound or type of compound that is less selectively adsorbed. The term "desorbent material" shall mean generally a material capable of desorbing an extract component. The term "raffinate stream" or "raffinate output stream" means a stream in which a raffinate component is removed from the adsorbent bed. The composition of the raffinate stream can vary from essentially 100% desorbent material to essentially 100% raffinate components. The term "extract stream" or "extract output stream" shall mean a stream in which an extract material which has been desorbed by a desorbent material is removed from the adsorbent bed. The composition of the extract stream, likewise, can vary from essentially 100% desorbent material to essentially 100% extract components. At least portions of the extract stream and the raffinate stream are passed to separation means, typically fractionators, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream. The term "rich" is intended to indicate a concentration of the indicated compound or class of compounds greater than 50 mole percent.

The rate of exchange of an extract component with the desorbent can generally be characterized by the width of the peak envelopes at half intensity obtained from plotting the composition of various species in the adsorption zone effluent during a pulse test versus time. The narrower the peak width, the faster the desorption rate. The rate of exchange of various components can be expressed as "stage time" which is calculated from the net retention volume and the half width peaks of the components according to the formula in *Principles of Adsorption and Adsorption Processes* by Douglas M. Ruthven, published by John Wiley & Sons, 1984. The desorption rate can also be characterized by the distance between the center of the tracer peak envelope and the disappearance of an extract component which has just been desorbed. This distance is the volume of desorbent pumped during this time interval.

Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope.

Relative selectivity can be expressed not only for one feed compound as compared to another but can also be expressed between any feed mixture component and the desorbent material. The selectivity, ($\beta$), as used throughout this specification is defined as the ratio of the two components in the adsorbed phase divided by the ratio of the same two components in the unadsorbed phase at equilibrium conditions. Relative selectivity is shown as Equation 1, below.

$$\text{Selectivity} = \frac{\text{wt. percent } C/\text{wt. percent } D_A}{\text{wt. percent } C/\text{wt. percent } D_U} \qquad \text{Equation 1}$$

where C and D are two components of the feed represented in weight percent and the subscripts A and U represent the adsorbed and unadsorbed phases, respectively. The equilibrium conditions are determined when the feed passing over a bed of adsorbent does not change composition, in other words, when there is no net transfer of material occurring between the unadsorbed and adsorbed phases.

Where selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity by the adsorbent of component C over component D, a $\beta$ larger than 1.0 indicates preferential adsorption of component C within the adsorbent. A B less than 1.0 would indicate that component D is preferentially adsorbed leaving an unadsorbed phase richer in component C and an adsorbed phase richer in component D.

While separation of an extract component from a raffinate component is theoretically possible when the selectivity of the adsorbent for the extract component with respect to the raffinate component is not much greater than 1, it is preferred that such selectivity approach a value of 2. Analogous to relative volatility in fractional distillation, the higher the selectivity, the easier the adsorptive separation is to perform. Higher selectivities permit a smaller amount of adsorbent to be used.

The "speed" of the adsorption steps at various conditions or for different adsorbent/desorbent combinations can be measured and compared as stage times. Stage times are normally inversely correlated with temperature. That is, as the temperature goes up, the stage times go down. A higher temperature is therefore normally desired since low stage times mean a smaller, less expensive plant is required to separate a given quantity of feed material. On the other hand selectivity is normally negatively impacted by higher temperatures. That is, selectivity decreases as the temperature goes up. In designing a commercial scale separation unit of this type, it is therefore necessary to choose operating conditions based upon a balance or trade-off of stage times versus selectivity.

As shown below the existence of an unexpected discontinuity in the stage time/selectivity/temperature has been discovered. This unexpected result allows one to operate at about 125° C. and obtain a balance of a good transfer rate and good selectivity. Above about 150° C. selectivities are declining without gaining a better transfer rate. At 100° C. poor transfer rates are obtained.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step.

The choice of desorbent materials used in adsorptive separation processes varies depending upon such factors as the type of operation employed. In adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component or both would complicate or prevent product recovery.

It has been discovered that employing a mixture of toluene and paradiethylbenzene as the desorbent results in an unexpected reduction in the required stage time. The truly synergistic result is not an average of the stage time of either desorbent and is below the stage time for either desorbent by itself.

Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. Therefore at least a portion of the desorbent material is normally separated from the extract and the raffinate streams of an adsorptive separation process by distillation or evaporation, but other separation methods such as reverse osmosis could also be employed alone or in combination with distillation or evaporation. Finally, desorbent materials should also be materials which are readily available and, therefore, reasonable in cost.

A dynamic testing "pulse test" apparatus may be employed to test adsorbents with a particular feed mixture and desorbent material to measure such adsorbent characteristics as adsorptive capacity, selectivity, resolution and exchange rate. The apparatus used herein consists of an adsorbent chamber of approximately 70 cc volume having inlet and outlet portions at opposite ends of the chamber. The chamber is contained within a temperature control means and pressure control equipment is used to operate the chamber at a constant predetermined pressure. Quantitative and qualitative analytical equipment such as refractometers, polarimeters and chromatographs can be attached to an outlet line of the chamber and used to detect quantitatively or determine qualitatively one or more components in the effluent stream leaving the adsorbent chamber. During a pulse test, the adsorbent is filled to equilibrium with a particular desorbent material by passing the desorbent material through the adsorbent chamber. The feed mixture, sometimes diluted in desorbent, is injected for a duration of several minutes. Desorbent flow is resumed, and the feed components are eluted as in a liquid-solid chromatographic operation. The effluent can be analyzed on-stream or, alternatively, effluent samples can be collected periodically and later analyzed separately and traces of the envelopes of corresponding component peaks developed.

From information derived from the test, adsorbent performance can be rated in terms of void volume, retention volume for an extract or a raffinate component, selectivity for one component with respect to the other, the resolution between the components and the rate of desorption of an extract component by the desorbent. The retention volume of an extract or a raffinate component may be determined from the distance between the center of the peak envelope of an extract or a raffinate component and the peak envelope of a tracer component or some other known reference point. It is expressed in terms of the volume in cubic centimeters of desorbent pumped during this time interval represented by the distance between the peak envelopes.

Retention volumes for good candidate systems fall within a range set by extrapolation to commercial designs. A very small retention volume indicates there is little separation between the two components. (One material is not adsorbed strongly enough.) Large extract retention volumes indicate it is difficult for the desorbent to remove the retained extract compound. In terms of the pulse test described herein retention volumes in the broad range of 30–90 cc's are desired.

In a commercial unit the adsorbent may be employed in the form of a fixed bed which is alternately contacted with the feed mixture and desorbent materials. In the simplest embodiment of the invention, the adsorbent is employed in the form of a single static bed in which case the process is only semicontinuous. In another embodiment, a set of two or more static beds may be employed with appropriate valving so that the feed mixture is passed through one or more adsorbent beds while the desorbent materials can be passed through one or more of the other beds in the set. The flow of feed mixture and desorbent materials may be either upward or downward through the adsorbent.

Any of the conventional apparatus employed in static bed fluid-solid contacting may be used in a commercial embodiment of the process. Countercurrent moving bed or simulated moving bed countercurrent flow systems, however, have a much greater separation efficiency than fixed adsorbent bed systems and are, therefore, preferred for commercial installations. One such moving bed system is described in U.S. Pat. No. 4,385,993. In the moving bed or simulated moving bed processes, the adsorption and desorption operations are continuously taking place which allows both continuous production of an extract and a raffinate stream and the continual use of feed and desorbent streams.

One preferred adsorbent contacting method utilizes what is known in the art as the simulated moving bed countercurrent flow system. The operating principles and sequence of such a flow system are described in U.S. Pat. No. 2,985,589 and 3,310,486, incorporated by reference herein. In such a system, it is the progressive movement of multiple liquid access points down an adsorbent chamber that simulates the upward movement of adsorbent contained in the chamber. Typically only four access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. To maintain the simulated movement, a liquid flow down the adsorbent chamber may be provided by a pump. As an active liquid access point moves through a cycle, that is, from the top of the chamber to the bottom, the chamber circulation pump provides different flow rates. A programmed flow controller may be provided to set and regulate these flow rates.

The active liquid access points effectively divide the adsorbent chamber into separate zones, each of which has a different function. It is generally necessary that three separate operational zones be present in order for the process to take place, although, in some instances, an optional fourth zone may be used. The zone numbers used in this description of a simulated moving bed process are those used and illustrated in U.S. Pat. Nos. 3,392,113 and 4,475,954 which are also incorporated herein by reference.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream, with respect to fluid flow in zone 1, is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet streams. The function of the desorbent zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams are advanced in the same direction through the adsorbent bed. Both the manifold arrangement and disc valve are known in the art. A multiple valve apparatus is described in detail in U.S. Pat. No.

4,434,051. Rotary disc valves which can be utilized in this operation are described in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which a desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by conduits. Input/output taps are attached at a number of locations with the active taps being periodically shifted to effect continuous operation.

In a commercial unit at least a portion of the extract output stream will pass into a separation means such as a fractionation column wherein a portion of the desorbent material can be recovered to produce an extract product containing a reduced concentration of desorbent material and a desorbent recycle stream. Preferably at least a portion of the raffinate output stream will also be passed to a separation means wherein a portion of the desorbent material is recovered to produce additional recycle desorbent and a raffinate product containing a reduced concentration of desorbent material. The design of such fractional distillation facilities will be dependent on the materials being separated, the desorbent composition, etc. An example for one aromatic hydrocarbon adsorptive separation process is provided by U.S. Pat. No. 5,177,295.

Another type of a simulated moving bed flow system suitable for use in the process of the present invention is the cocurrent high efficiency simulated moving bed process disclosed in U.S. Pat. Nos. 4,402,832 and 4,478,721 to Gerhold, incorporated by reference herein in its entirety. This process may be preferred, because of its energy efficiency and lower capital costs, where products of slightly lower purity are acceptable.

Although both liquid and vapor phase operations can be used in many adsorptive separation processes, liquid-phase operation is preferred for this process because of the nature of the materials being separated. Adsorption conditions can include a temperature range of from about 20° to about 200° C., with 100° to about 150° C. being more preferred and 100° to 125° C. being highly preferred. Adsorption conditions also include a pressure range of from about atmospheric to about 500 psig as required to insure liquid phase operations with pressures from about atmospheric to about 250 psig being preferred. Increased temperature tends to reduce retention volumes. Desorption conditions preferably include the same temperature and pressure as used for adsorption.

The size of the units which can utilize the process of this invention can vary anywhere from those of pilot plant scale (see, for example, U.S. Pat. No. 3,706,812 assigned to UOP) to those of commercial scale and can range in flow rates from as little as a few cc's an hour up to many thousands of gallons per hour.

The examples shown below are intended to further illustrate the process and discoveries of this invention and are not to be construed as unduly limiting the scope and spirit of said process. The examples present test results for various adsorbent and desorbent materials and conditions determined using the previously described dynamic pulse test method.

EXAMPLE 1

The effect of temperature on process performance was determined in experiments performed at otherwise uniform conditions including a superficial velocity in the adsorbent bed of 1.12 cm/minute. The adsorbent was cesium exchanged X zeolite. The desorbent was para-diethylbenzene. The tests were performed using a 2 cc feed pulse over a 70 cc adsorption column. In all of the tests of this example the feed pulse contained an admixture of equal quantities of para-xylene, ortho-xylene, meta-xylene, ethylbenzene and normal $C_9$ paraffins. The adsorbent was a zeolite X having a silica to alumina ratio of 2.0:1. Table 1 below presents a summary of the selectivities, $\beta$, of ethylbenzene versus the xylene components of the feed pulse.

A review of the data in Table 1 reveals that selectivities are better at lower temperatures as shown by the selectivity at 100° C. However, the benefits of operating at lower temperatures have to be weighed against the detriment of lower temperatures. The most significant disadvantage of operating at lower temperatures is a decrease in the transfer rate of the various feed components versus the adsorbent. The decrease in transfer rates results in a broadening of the adsorption profile or envelopes of the individual components. This results in more overlap of the envelopes for any one set of conditions. An overlap of the envelope means that two or more components will be present in the portion of the extract stream subject to the overlap and the purity of the various streams will decrease. To compensate for this it is necessary to increase the amount of adsorbent which is used to perform the separation with the same degree of separation. This is turn increases the cost of the process.

Table 2 presents the stage time for p-xylene and ethylbenzene at the same temperatures as for the data given in Table 1. The discontinuity or shelf in the stage times between 125° and 150° C. is evident from this data.

TABLE 1

| Temp | Selectivity vs. Temperature | | | Stage Time |
|---|---|---|---|---|
| | Selectivity | | | |
| °C. | EB | p-xylene | o-xylene | p-xylene |
| 100 | 1.0 | 2.77 | 1.96 | 23.7 |
| 125 | 1.0 | 2.30 | 1.84 | 22.4 |
| 150 | 1.0 | 2.05 | 1.61 | 22.4 |
| 175 | 1.0 | 1.84 | 1.38 | 13.3 |

TABLE 2

| Temp °C. | Stagetime vs. Temperature | |
|---|---|---|
| | p-xylene | ethylbenzene |
| 100 | 23.7 | 26.3 |

TABLE 2-continued

Stagetime vs. Temperature

| Temp °C. | p-xylene | ethylbenzene |
|---|---|---|
| 125 | 22.4 | 21.2 |
| 150 | 22.4 | 21.6 |
| 175 | 13.3 | 19.7 |

TABLE 3

Selectivity vs. Desorbent

| | Selectivity | | |
|---|---|---|---|
| Desorbent | p-xylene | m-xylene | o-xylene |
| cumene | 2.45 | 3.23 | 2.07 |
| propyl-benzene | 2.02 | 3.49 | 2.23 |
| toluene | 1.75 | 2.4 | 2.14 |
| p-diethyl-benzene | 2.77 | 2.99 | 1.96 |

EXAMPLE 2

A number of experiments were performed to measure the performance of different desorbents. The adsorbent was zeolite X having a silica to alumina ratio of 2.0:1. The zeolite had been exchanged with cesium to obtain an approximate 54 % cesium ion content. The desorbent was varied as listed in Table 3. The tests were performed at 100° C. using a 2 cc feed pulse in a 70 cc adsorption column. In all of the tests of this example the feed pulse contained an admixture of equal quantities of para-xylene, orthoxylene, meta-xylene, ethylbenzene and normal $C_9$ paraffins. Table 3 summarizes the measured selectivities of ethylbenzene adsorption versus the significant components of the feed pulse.

The strength of the desorbent is an important factor in the success of a selective adsorption process. For instance a stronger desorbent may allow the use of a more selective adsorbent having an otherwise unacceptably high product retention volume. Toluene and p-diethylbenzene are the preferred desorbents on an economic basis centered on their costs. The data of Table 3 illustrates that toluene also provides good selectivities. It has an added advantage in that it has a low net retention volume of 12.3 ml. Paradiethylbenzene has the advantage of a better selectivity than toluene but has a poor (high) net retention volume of 33.1 ml.

EXAMPLE 3

Experiments were performed in an attempt to obtain a desorbent composition providing both a good net retention volume and high selectivities. The tests were performed using a 2 cc feed pulse over a 70 cc adsorption column operated at 125° C. and loaded with zeolite X having a silica to alumina ratio of 2.0:1 with 54 % of the exchangeable cites containing cesium ions. In the tests of this example the feed pulse contained an admixture of equal quantities of para-xylene, ortho-xylene, meta-xylene, ethylbenzene and nonane.

With a desorbent mixture containing 50 volume % of toluene and p-diethylbenzene the net retention volume of ethylbenzene was 17.9 ml and the selectivities versus para, meta and ortho xylene respectively were 1.86, 2.57 and 2.10.

With a desorbent containing a 30/70 volume % mixtures of toluene and diethylbenzene the ethylbenzene net retention volume was 22 and the selectivity versus the three xylenes was 2.04, 2.92 and 2.26.

Even more interesting and unexpected is the synergistic results of a decreased ethylbenzene stage time seen at ethylbenzene concentrations greater than 50 vol.%. The Table below presents this data for various p-DEB/toluene mixtures.

TABLE 4

Stage Time vs. Desorbent

| % pDEB | Stage Time |
|---|---|
| 0 | 18.7 |
| 50 | 21.3 |
| 70 | 14.5 |
| 100 | 21.2 |

EXAMPLE 4

Ion exchange of a zeolitic adsorbent can have a great influence on the performance of the adsorbent. For this reason, a number of tests were conducted to investigate the impact of the level of cesium exchange on the performance of zeolite X. These tests were performed at 100° C. using 100 vol.% toluene as the desorbent and a 2 cc four-component feed pulse in a 70 cc adsorbent bed. The level of cesium replacement of the native sodium was varied from about 25 to about 64 mole percent. Based on the results of these tests, it was determined that ethylbenzene selectivity versus meta and orthoxylene increased as the amount of cesium exchange increased, with the rate of increase accelerating after 50% cesium was present on the sieve. However, the ethylbenzene selectivity versus paraxylene decreased after the cesium level of the sieve exceeded 50%. It was also determined that net retention volumes for all of the four feed components except paraxylene began to decrease after about 56 mole percent cesium was present on the sieve. Based on this data, it is preferred that the sieve is exchanged to contain more than 50 mole percent cesium and more preferably less than 60 mole percent cesium in its exchangeable sites.

One embodiment of the invention may accordingly be characterized as a continuous process for separating ethylbenzene from a mixture comprising ethylbenzene and at least one xylene, which process comprises contacting said mixture at adsorption conditions with an adsorbent comprising zeolite X which has been exchanged with cesium ions at between 50 and 60% of the zeolites exchangeable sites and has a silica:alumina ratio of about 2.0, selectively adsorbing said ethylbenzene, removing the nonadsorbed portion of said mixture from contact with said adsorbent and recovering ethylbenzene by desorption with a desorbent comprising at least 25 vol.% toluene and at least 50 vol.% p-diethylbenzene at desorption conditions. In this mixed desorbent embodiment, it is preferred that the desorbent contain at least about 25 vol.% each of toluene and diethylbenzene, with at least 50 vol.% p-diethylbenzene being highly preferred. It is more preferred that the desorbent contain from 30 to 50 vol.% toluene and at least about 50 to 70 vol.% diethylbenzene.

What is claimed is:

1. A process for separating ethylbenzene from a mixture comprising ethylbenzene and at least one other $C_8$ aromatic hydrocarbon, which process comprises contacting said mixture at adsorption conditions including a temperature between about 100° and about 125° C. with an adsorbent comprising a cesium exchanged zeolite X having a silica:alumina ratio from 2.0:1.0 to 2.3:1.0, selectively adsorbing said ethylbenzene, removing the nonadsorbed portion of said mixture from contact with said adsorbent and recovering ethylbenzene by desorption with a desorbent comprising para-diethylbenzene at desorption conditions.

2. The process of claim 1 wherein said desorbent also comprises toluene.

3. The process of claim 3 wherein said desorbent comprises at least 25 vol. % toluene.

4. A process for separating ethylbenzene from a mixture of ethylbenzene and at least one other xylene which comprises contacting said mixture with an adsorbent comprising a zeolite X having a silica:alumina ratio less than about 2.2:1.0 and having been ion-exchanged to contain cesium at more than 40 percent of the zeolites exchangeable sites, selectively adsorbing said ethylbenzene onto said zeolite, and then removing the nonadsorbed portion of said mixture from contact with said adsorbent and recovering said ethylbenzene from said zeolite by desorption with a desorbent comprising an admixture of toluene and paradiethylbenzene at desorption conditions.

5. The process of claim 4 wherein the desorbent comprises at least 50 vol.% p-diethylbenzene.

6. The process of claim 4 wherein the zeolite has a silica:alumina ratio less than 2.1:1.

7. A continuous process for separating ethylbenzene from a mixture comprising ethylbenzene and at least one xylene, which process comprises contacting said mixture at adsorption conditions including a temperature of from about 100° to about 125° C. with an adsorbent comprising zeolite X which has been exchanged with cesium ions at between 50 and of the zeolites exchangeable sites and has a silica:alumina ratio of about 2.0, selectively adsorbing said ethylbenzene, removing the nonadsorbed portion of said mixture from contact with said adsorbent and recovering ethylbenzene by desorption with a desorbent comprising at least 25 vol.% toluene and at least 50 vol.% p-diethylbenzene at desorption conditions.

8. The process of claim 7 wherein said desorbent comprises at least 25 vol. % toluene.

9. The process of claim 7 wherein said desorbent comprises from 30 to 50 vol.% toluene and at least about 50 to 70 vol.% p-diethylbenzene.

* * * * *